(12) United States Patent
Furey

(10) Patent No.: US 10,258,344 B2
(45) Date of Patent: Apr. 16, 2019

(54) MEDICAL FILAMENT DELIVERY APPARATUS

(71) Applicant: COOK MEDICAL TECHNOLOGIES LLC, Bloomington, IN (US)

(72) Inventor: Aidan Furey, Valby (DK)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 86 days.

(21) Appl. No.: 15/447,951

(22) Filed: Mar. 2, 2017

(65) Prior Publication Data

US 2017/0252046 A1 Sep. 7, 2017

(30) Foreign Application Priority Data

Mar. 2, 2016 (GB) .................................. 1603633.7

(51) Int. Cl.
*A61B 17/00* (2006.01)
*A61B 17/12* (2006.01)
(52) U.S. Cl.
CPC .... *A61B 17/12181* (2013.01); *A61B 17/1214* (2013.01); *A61B 17/12031* (2013.01);
(Continued)
(58) Field of Classification Search
CPC .. A61B 2017/12054; A61B 2017/1205; A61B 17/12109; A61B 17/12113; A61B 17/12118; A61B 17/0467
See application file for complete search history.

(56) References Cited

U.S. PATENT DOCUMENTS 5,476,472 A 12/1995 Dormandy, Jr. et al.
6,379,329 B1 4/2002 Naglreiter et al.
(Continued)

FOREIGN PATENT DOCUMENTS

EP 2875788 A1 5/2015
EP 2 952 144 A1 12/2015

OTHER PUBLICATIONS

EP 17275018.4-1664, Communication—Extended European Search Report, dated Jul. 18, 2017.
(Continued)

*Primary Examiner* — Wade Miles
(74) *Attorney, Agent, or Firm* — Brinks Gilson & Lione

(57) ABSTRACT

Medical filament delivery apparatus includes a feed chamber to which can be fed filamentary material from a store of filamentary material. The apparatus is designed to feed filamentary material through a catheter into a patient, for example into an aneurysm. The apparatus includes a feed tube assembly having a feed tube with a slot at its distal end. A distal end of the filamentary material can be held within the slot to ensure accurate positioning of the distal end of the filamentary material into the drive assembly. The apparatus provides for severing of the distal end of the filamentary material once the feed tube assembly has been inserted into the drive assembly, thereby ensuring reliable positioning of the filamentary material into the drive assembly. More delicate filamentary material can be handled compared to prior art arrangements.

19 Claims, 8 Drawing Sheets

(52) U.S. Cl.
CPC .. *A61B 17/12113* (2013.01); *A61B 17/12118* (2013.01); *A61B 2017/00477* (2013.01); *A61B 2017/1205* (2013.01); *A61B 2017/12054* (2013.01)

(56) References Cited

U.S. PATENT DOCUMENTS

| | | | |
|---|---|---|---|
| 6,458,137 | B1 | 10/2002 | Klint |
| 6,964,657 | B2 | 11/2005 | Cragg et al. |
| 9,788,831 | B2 * | 10/2017 | Mitelberg .......... A61B 17/0487 |
| 2003/0225391 | A1 | 12/2003 | Cragg et al. |
| 2007/0270907 | A1 * | 11/2007 | Stokes ............... A61B 17/0469 606/232 |
| 2008/0234729 | A1 * | 9/2008 | Page .................. A61B 17/0485 606/232 |
| 2011/0077681 | A1 | 3/2011 | Nagano et al. |
| 2013/0296917 | A1 | 11/2013 | Rees |
| 2015/0351774 | A1 | 12/2015 | Furey et al. |

OTHER PUBLICATIONS

GB1603633.7 Combined Search and Examination Report dated Aug. 5, 2016.
European Examination Report for EP 17275018.4-1664, dated Dec. 12, 2017.

\* cited by examiner

MEDICAL FILAMENT DELIVERY APPARATUS

CROSS-REFERENCE TO RELATED APPLICATIONS

This application claims the benefit of priority under 35 U.S.C. § 119(a) to Great Britain Patent Application No. GB 1603633.7, filed Mar. 2, 2016, which is hereby incorporated by reference in its entirety.

TECHNICAL FIELD

The present invention relates to apparatus for delivering filamentary material into a patient and to a device for guiding filamentary material through such apparatus. The filamentary material can be used to fill an aneurysm, occlude a vessel or other organ, as well as for other medical procedures.

BACKGROUND ART

There are several medical conditions which can benefit from implantation into a patient of a filler material, an embolization coil or other device, whether temporary or permanent. Examples include the closure of blood vessels or other lumens. One condition for which such procedures can be particularly useful is in the treatment of aneurysms, where a part of a vessel wall weakens and expands outwardly to create an enlarged zone of the vessel, often having the form of a sac. This vessel expansion occurs as a result of blood pressure and tends to continue due to further and progressive weakening of the vessel wall. If left untreated, persistent pressure from the blood flow on the weakened wall tissue can lead to eventual rupture of the vessel and consequential haemorrhaging. Treatments for aneurysms have tended to focus on reducing the pressure on the weakened vessel wall, for instance by diverting blood flow or by isolating the weakened vessel wall, for instance by means of a stent graft. Another treatment method involves filling the aneurysm sac with a filler material which stops the flow of blood into the sac and as a result stops or substantially reduces the pressure on the weakened walls. The filler may be an embolization coil, which will cause static blood around the embedded coil to clot, which blocks the sac and creates a protective barrier to prevent vessel rupture. In other methods the aneurysm may be filled with a biocompatible material, such as a hydrogel or a polysaccharide fibre, which may be of a biodegradable nature. A biodegradable filler performs the same function as an embolization coil, that is to fill the aneurysm sac and provide pressure protection to the weakened vessel walls, with the additional advantage of allowing remodeling of the vessel wall over time. Moreover, biodegradation of the filler will ensure that no foreign matter remains in the patient's vessel after conclusion of the treatment.

A useful technique involves the administration of a filamentary filler material, which can be delivered endoluminally through a small diameter catheter. The filamentary material is biocompatible and potentially also biodegradable. In many instances it is optimal to use filamentary material having a very small diameter, which enables the use of a narrow diameter delivery catheter, useful for delivery through and into small diameter vessels, for filling small aneurysm sacs, and so on. However, narrow diameter filaments can be difficult to handle, both into the delivery apparatus and from the delivery apparatus into the delivery catheter. Similar problems can also be encountered with biological or similar filamentary material, such as material made from small intestine submucosa (SIS), which can be difficult to handle especially in filamentary form.

Examples of endoluminal filament and coil delivery systems can be found in U.S. Pat. No. 6,458,137, U.S. Pat. No. 5,476,472, U.S. Pat. No. 6,379,329, US-2003/0225391, US-2011/0077681 and US-2013/0296917.

DISCLOSURE OF THE INVENTION

The present invention seeks to provide improved delivery of filamentary material into a patient and improved apparatus therefore.

According to an aspect of the present invention, there is provided medical filament delivery apparatus including: a filament drive unit provided with a feed chamber, a first inlet to the feed chamber connectable to a fluid supply, a second inlet to the feed chamber connectable to a supply of filamentary material, and an outlet from the feed chamber attached or attachable to a delivery catheter; a tubular guide element disposed or disposable at least partially within the feed chamber and between the second inlet and the outlet; the guide element including a tubular structure with an internal lumen, the tubular guide element including a proximal end and a distal end, the proximal end having an inner first diameter; and an elongate filamentary material feed tube including a distal end having an outer second diameter, wherein the feed tube distal end is insertable into the proximal end of the tubular guide element, such that filamentary material from the feed tube is able to pass into the tubular guide element; the feed tube including a fixation member for fixing an end of filamentary material to or proximate the feed tube distal end, the fixation member providing for release of the fixed end of the filamentary material on insertion of the feed tube distal end into the proximal end of the tubular guide element.

It can be problematic to feed the first end of filamentary material into the delivery apparatus and the structure disclosed herein provides a solution to experienced problems. The feed tube holds the end of the filamentary material, ensuring that it is appropriately positioned into the delivery apparatus, in this case in the tubular guide element, and also provides for release of the end of filamentary material when in the assembled condition, such that the filamentary material can be dispensed into the patient. The apparatus provides a mechanism which can ensure that the end of the filamentary material is not lost during assembly of the apparatus.

The fixation member preferably provides for release of the filamentary material by severing of the fixed end of the material. The process of release of the distal end of the filamentary material can therefore be simple and reliable, preferably requiring no specific action on the part of the physician beyond putting the component parts of the assembly together.

In a preferred embodiment the fixation member is a slot or hole at the feed tube distal end, wherein the end of the filamentary material is trappable in the slot or hole. Advantageously, the feed tube distal end is a close fit in the proximal end of the tubular guide element, such that filamentary material trapped in the slot or aperture is cut, or severed, when the feed tube distal end is inserted into the proximal end of the tubular guide element. This structure provides a simple, effective and automatic mechanism for releasing the distal end of the filamentary material as the feed tube is fitted into the guide tube. No other action is required by the user and there is no risk of the user prematurely releasing the filamentary material. Furthermore, the structure ensures correct positioning of the filamentary material into the delivery apparatus for reliable delivery into a patient.

In the preferred embodiment, the tubular guide element includes at least one aperture therein, the at least one aperture allowing fluid in the feed chamber to flow into the internal lumen thereof. In a practical example, the tubular guide element is a cannula provided with a plurality of apertures therein.

Advantageously, the apertures in the tubular guide element extend generally in a longitudinal direction of the tubular guide element. The apertures provide for supply of delivery fluid directly into the guide element and to the filamentary material held therein.

There is preferably provided a dispenser of filamentary material, the feed tube being coupled to the dispenser. The feed tube may be attached to a casing of the dispenser and supported thereby.

Advantageously, the feed tube and the second inlet of the drive unit include cooperating fixation members for fixing the feed tube to the drive unit.

There is preferably provided a sealing element at the outlet and/or inlet of the filament drive unit, whereby fluid exits the feed chamber via the lumen of the tubular guide element.

In an embodiment, the proximal end of the tubular guide element extends beyond the second inlet of the filament drive unit. Similarly, the distal end of the tubular guide element may extend beyond the outlet of the filament drive unit. Preferably, a delivery catheter is coupled to the outlet of the filament drive unit, wherein the proximal end of the tubular guide element extends into the delivery catheter.

Preferably, the tubular guide element is fitted to a coupling member, the coupling member being attachable to the filament drive unit. The coupling member may be attachable at the outlet of the filament drive unit. In some embodiments at least, the coupling member may be disposed at an intermediate position along a length of the tubular guide element.

There is also described a method of delivering filamentary material into a vessel or other organ of a patient by means of delivery apparatus including:

a filament drive unit provided with a feed chamber, a first inlet to the feed chamber connectable to a fluid supply, a second inlet to the feed chamber connectable to a supply of filamentary material, and an outlet from the feed chamber attached or attachable to a delivery catheter;

a tubular guide element disposed or disposable at least partially within the feed chamber and between the second inlet and the outlet; the guide element including a tubular structure with an internal lumen, the tubular guide element including a proximal end and a distal end, the proximal end having an inner first diameter; and an elongate filamentary material feed tube including a distal end having an outer second diameter, the feed tube including a fixation member which fixes an end of filamentary material to or proximate the feed tube distal end;

the method including the steps of:

inserting the feed tube distal end into the proximal end of the tubular guide element, such that filamentary material from the feed tube is able to pass into the tubular guide element, wherein said insertion causes release of the fixed end of the filamentary material; and supplying driving fluid into the feed chamber, said driving fluid driving said filamentary material into and through the delivery catheter.

Advantageously, insertion of the feed tube distal end into the proximal end of the tubular guide element severs the fixed end of the material.

The method may include the step of supplying fluid to the supply of filamentary material. This fluid can be used to wet the filamentary material and/or as a second source of driving fluid.

Other features, aspects and advantages of the apparatus disclosed herein will become apparent from the specific description which follows.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Preferred embodiments of the apparatus taught herein are described below and shown in the accompanying drawings. The skilled person will appreciate that the drawings are not to scale and also that minor elements and features of the apparatus familiar in the art but not relevant to the teachings herein are not shown or described for the sake of conciseness and clarity.

The embodiments described herein are shown arranged for delivering long lengths of filamentary material into a patient. The nature of the material is not relevant to the disclosures herein but it may preferably be of SIS (small intestine submucosa), polysaccharide, a biocompatible polymeric thread or other biocompatible material. The apparatus is suitable for delivering material of small diameter through a small diameter delivery catheter. It can also be used for large diameter material and catheters.

Figure 1:
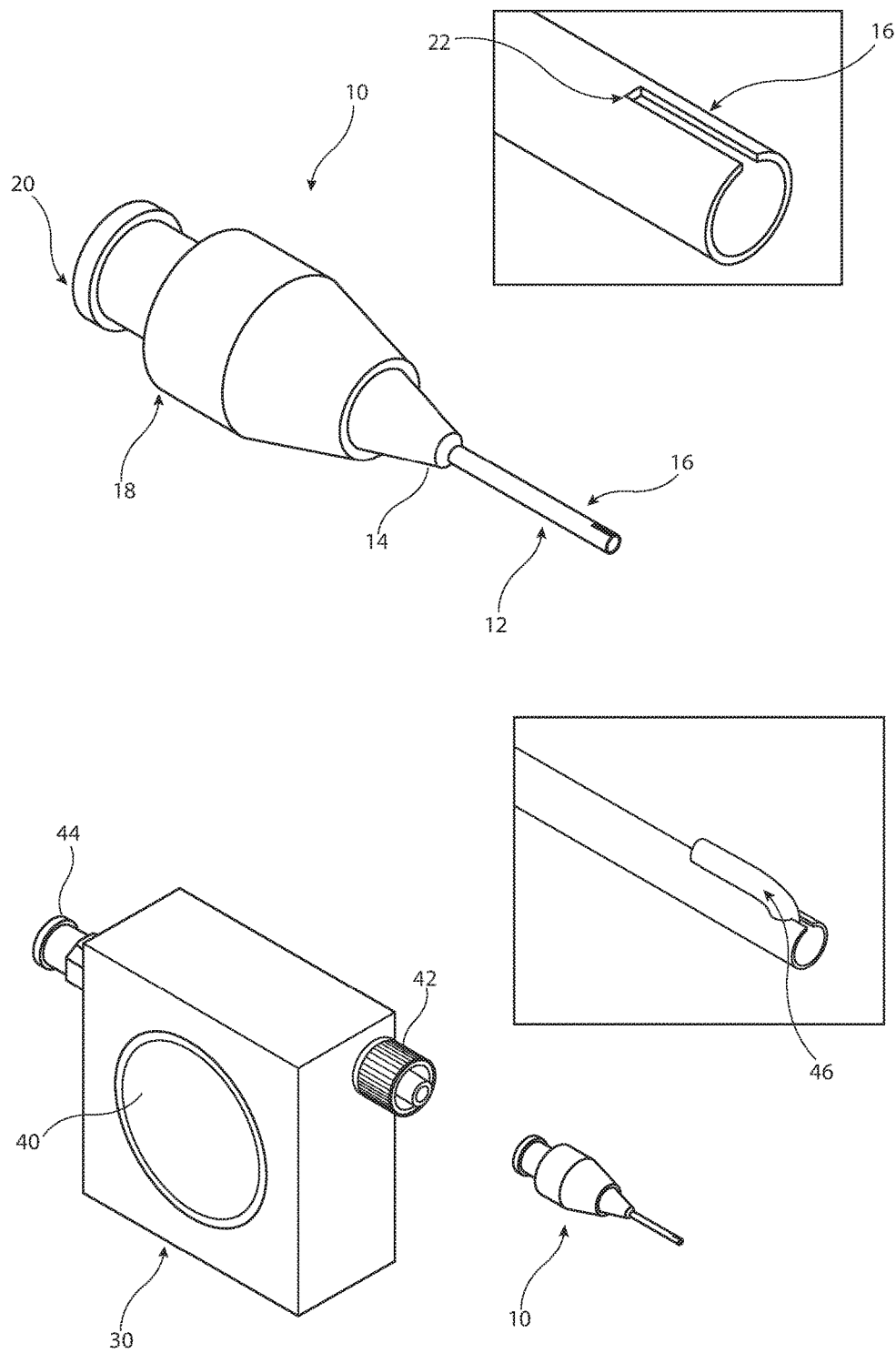
FIG. 1 shows various views of a distal end of the feed tube of the preferred embodiment of apparatus.

Referring first to FIG. 1, this shows various views of the feed tube assembly 10 of the preferred embodiment of apparatus taught herein. The assembly 10 includes an elongate feed tube member 12 for holding and feeding filamentary material into the delivery apparatus, as described below in detail. A luer fitting 18 is attached at the distal end of the feed tube member 12 and includes a luer lock 20 of conventional form. A lumen extends through the luer fitting 10 and the feed tube member 12.

At the distal end 16 of the feed tube member 12 there is located a slit 22 having a diameter preferably just smaller than the diameter of filamentary material intended to be held in and fed through the feed tube assembly 10. The slit 22 has a length at least as great as the diameter of the filamentary material, though it is to be understood that the length of the slit 22 is not critical.

The feed tube 12 is preferably rigid and may be made of a metal, metal alloy, rigid plastics, ceramic or other suitable material. The luer lock assembly 18 may typically be made of a plastics material or of metal or metal alloy.

With reference to the lowermost drawing in FIG. 1, a filament storage device 30 is shown, in which a length of filamentary material 40 (seen better in FIG. 6) is, in this example, held on a cylindrical drum, which preferably has a helical groove running across its outer surface, such that individual turns of the filamentary material 40 are held separated from one another by the turns of the helical groove. The filament storage device 30 includes a male luer fitting 42 at an outlet of the device 30 and a female luer fitting 44 at an inlet of the device. The luer fitting 44 can be used to supply further filamentary material 40 into the storage device in cases where this is needed and/or to supply wetting fluid (for example saline solution). As will be apparent, the luer fitting 18 can be locked into the outlet luer fitting 42 of the filament storage device 30 and such that the lumen therein aligns with the lumen within the outlet fitting 42, such that filamentary material 40 can pass from the storage device 30 into the feed tube assembly 10. Typically, the feed tube assembly 10 is attached to the filament storage device 30 during assembly and such that the distal end 46 of the filamentary material 40 can be trapped into the slot 22 and pulled back on itself so that the distal end 46 of the filamentary material points in a proximal direction (in practice, as will be apparent below, in a direction away from the direction of insertion of the feed tube assembly 10 into the delivery assembly).

The feed tube 12 and the lumen therein (and similarly the other lumens of the apparatus) are preferably circular in transverse cross-section in order to accommodate the filamentary material, which in the preferred embodiments is made of a relatively soft fibrous material.

Figure 2:
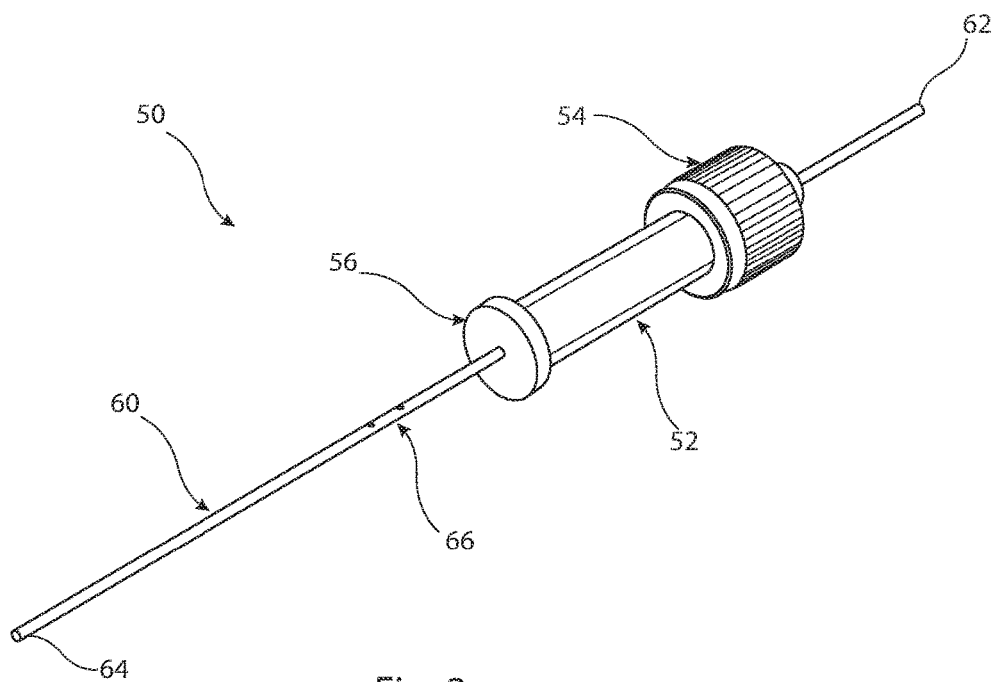
FIG. 2 shows a preferred embodiment of the tubular guide element of the delivery apparatus.

Referring now to FIG. 2, this shows a perspective view of the tubular guide element 50 of the delivery apparatus. The guide element 50 includes a double luer fitting 52 having at one end a catheter luer lock 54 and at the other end a Y-fitting luer lock 56. Integral with the double luer fitting 52 is a tubular guide member 60 which extends through the double luer fitting 52 and includes a distal end 62 and a proximal end 64. The tubular guide member 60 may be made of a metal or hard plastics material, or other suitable material. It may be made of the same material as the elongate feed tube 12.

The tubular guide member includes a plurality of flushing holes 66 proximal of the Y-fitting lock 56 and spaced from one another in the longitudinal direction of the tubular guide member 60. In FIG. 2 there are shown two flushing holes 66 in the tubular guide member 60 but the number of flushing holes may vary.

Figure 3:
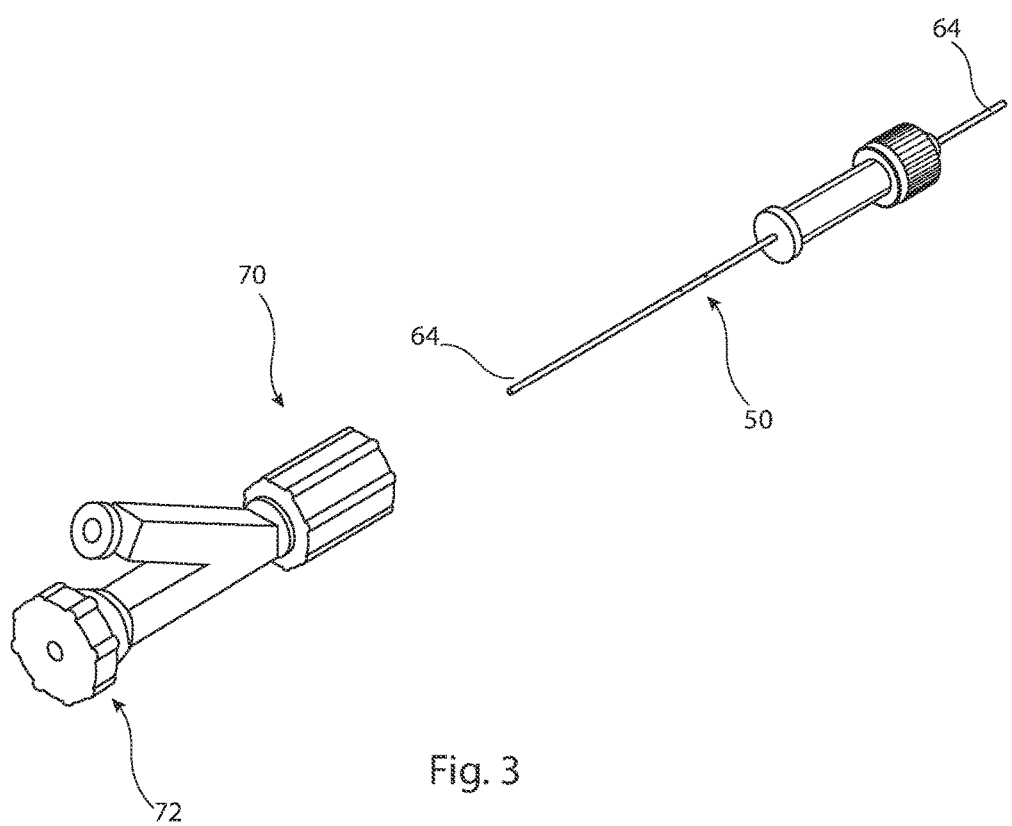
FIG. 3 shows how the tubular guide element can be fitted to a standard Y-fitting.
Figure 4:
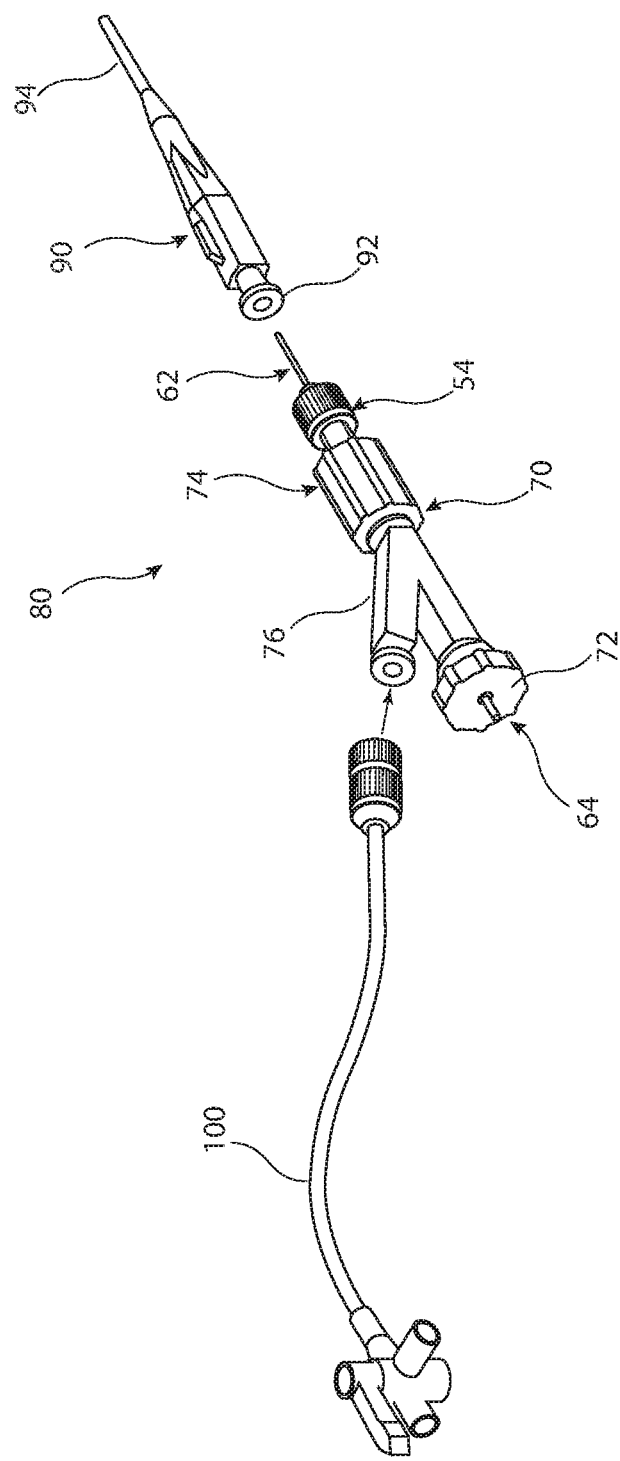
FIG. 4 is a perspective view of the major part of the delivery apparatus of the preferred embodiment.

Referring to FIG. 3, the tubular guide assembly 50 is designed to fit within a standard Y-fitting 70 and such that the guide tube 60 passes through the main body of the Y-fitting 70, the tube 60 being long enough to extend beyond the proximal end 72 of the Y-fitting 70, as will be apparent from FIG. 4. For this purpose, the guide tube 60 has an outer diameter which is preferably a close fit to seal in the Y-fitting 70.

Referring to FIG. 4, this shows the major components of the fluid delivery section of the filament delivery apparatus 80. In FIG. 4, the tubular guide assembly 50 has been inserted into the Y-fitting 70, with its Y-fitting connector 56 locked into the luer connector 74 of the Y-fitting 70. The guide tube 60 extends, as explained above, through the main body of the Y-fitting 70 and beyond the proximal end 72 of the Y-fitting 70, such that the proximal end 64 of the guide member 60 is exposed. The distal end 62 of the tubular member 60 extends in a distal direction and in practice so as to fit within a lumen 92 of a catheter assembly 90. The catheter assembly 90 includes a catheter element 94, typically of sufficient length to be able to be fed endoluminally through a patient's vasculature from a remote percutaneous entry point and up to the site within the patient at which the filamentary material is to be delivered. In some embodiments the catheter assembly 90 may be integral with the Y-fitting 70. In some embodiments the catheter 94 may be of a small diameter, that is a micro-catheter.

The side arm 76 is in use attached, in this example, to a feed catheter assembly 100 which can be connected to a supply of driving fluid, for instance saline solution.

Figure 5:
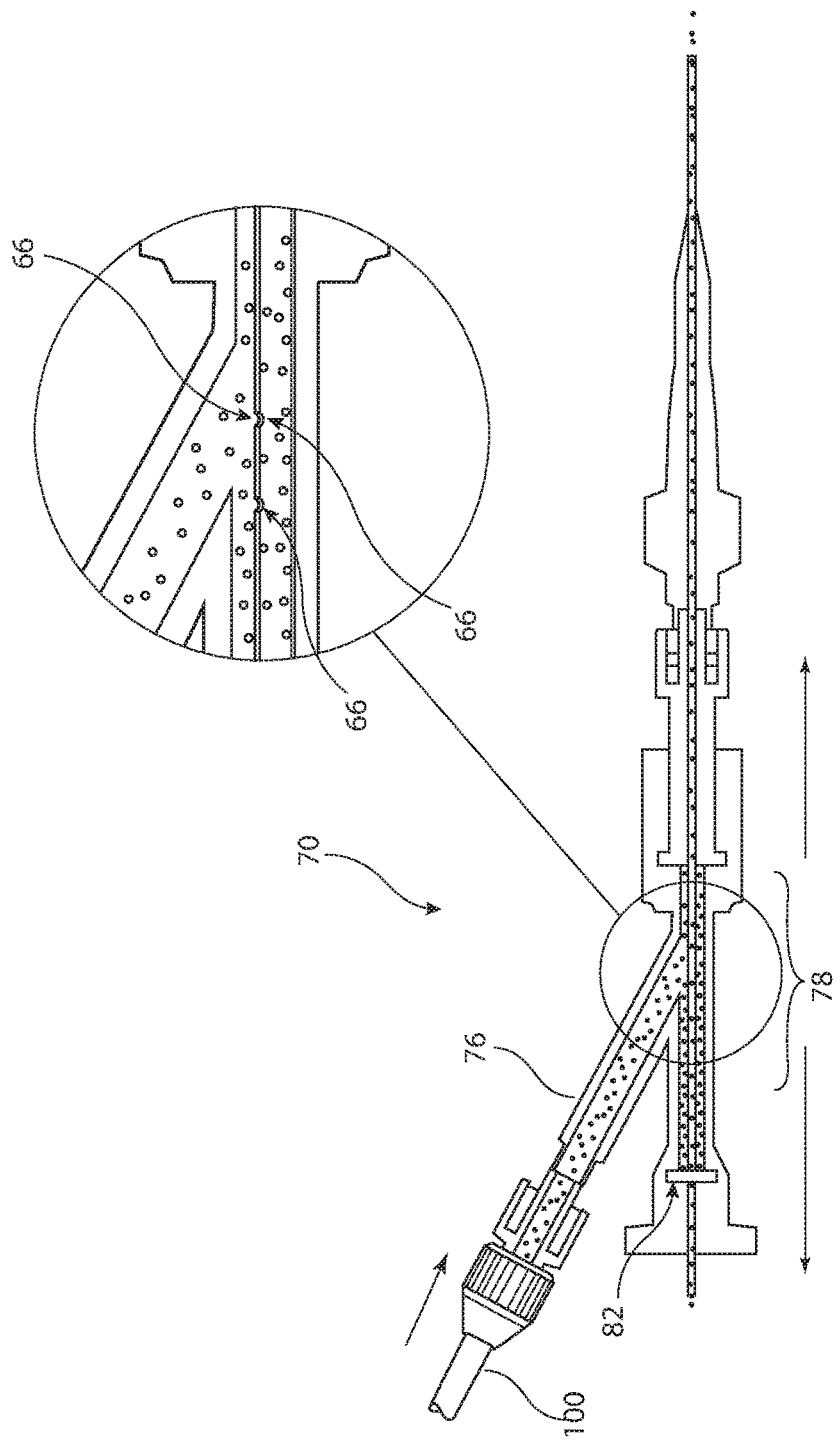
FIG. 5 is a partial cross-sectional view showing the flow of driving fluid through the components of the delivery apparatus.

With reference now to FIG. 5, this shows two cross-sectional views of the assembly of FIG. 4. Driving fluid from the feed catheter 100 into the side arm 76 of the wire fitting 70 is depicted by the black dots in FIG. 5. The Y-fitting 70 provides what could be described as a feed chamber 78 of the apparatus. The Y-fitting 70 includes a disk valve 82 at its proximal end 72, through which the proximal end 64 of the guide tube 60 can pass. The valve 82 delimits one end of the feed chamber 78. A valve similar to the valve 82, located at the distal end 74 of the Y-fitting 70 (but not visible in FIG. 5), is located at the distal end of the feed chamber 78. In this manner, fluid passing into the feed chamber 78 from the side arm 76 is trapped within the feed chamber 78, apart from being able to pass into the tubular guide member 60 via the apertures 66. As can be seen in the enlarged section of FIG. 5, the apertures 66 are preferably located at the junction with the side arm 76. In this manner, drive fluid under pressure fed into the side arm 76 will pass into the lumen of the tubular guide member 60 and therefrom through the catheter 94. As the skilled person will understand, fluid in the catheter 94 will pull filamentary material through the catheter 94, until it is dispensed from the distal end of the catheter 94.

Figure 6:
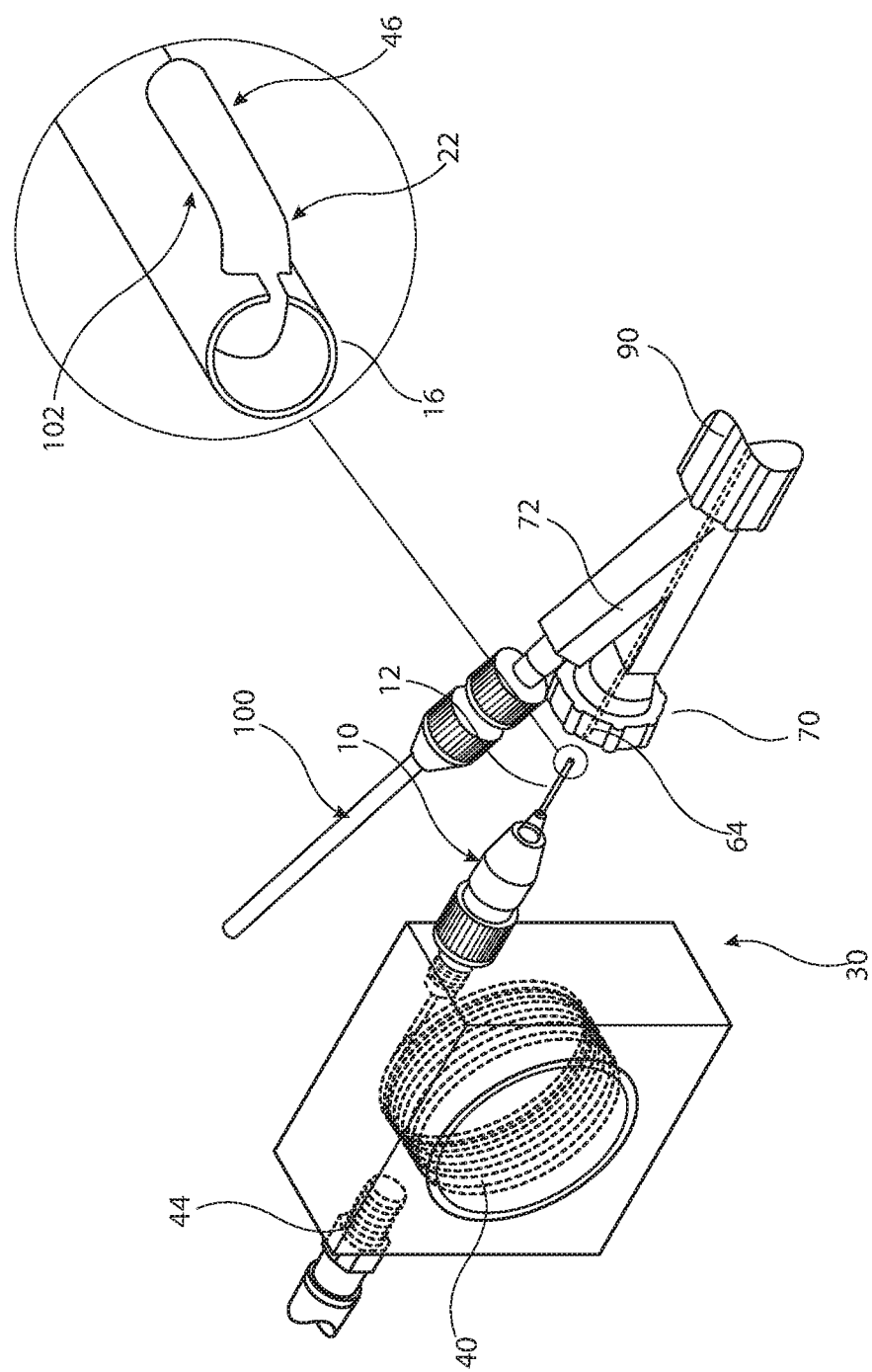
FIG. 6 is a perspective view in partial cross-section of an example dispenser of filamentary material for attachment to the delivery apparatus.

With reference now to FIG. 6, this shows how the feed tube assembly 10 and the filament storage device 30 are connected to the other components of the delivery apparatus. With reference first to the enlarged section of FIG. 6, the distal end 46 of the filamentary material 40, held within the slot 22, may be fixed to the outside surface of the feed tube 12, for instance by a spot of adhesive 102.

The distal end 16 of the feed tube 12 can be slid into the proximal end 64 of the tubular guide member 60. The arrangement is such that the feed tube 12 and the tubular guide member 60 are a close fit one within the other. Specifically the outer diameter of the feed tube 12 is designed to be about the same or only slightly smaller than the inner diameter of the guide tube 60, such that when the feed tube 12 is inserted into the guide tube 60 the distal end 46 of the filamentary material 40 is severed, in practice releasing the filamentary material 40 from its attachment to the feed tube 12, enabling it to move out of the feed tube 12 for delivery in to a patient.

Figure 7:
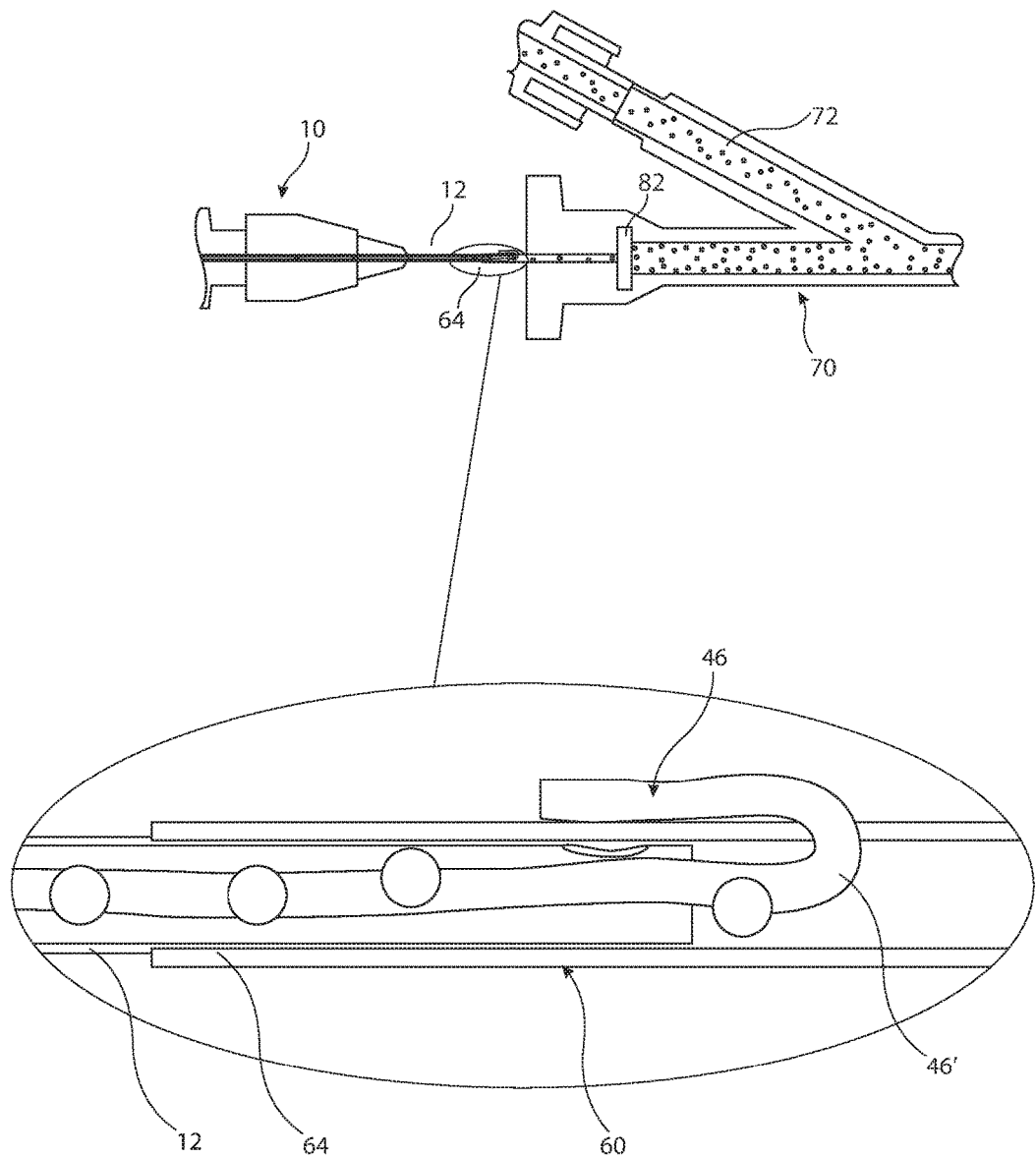
FIG. 7 is a side elevational view in partial cross-section showing the connection between the delivery tube and the tubular guide element of the preferred embodiment of apparatus.

FIG. 7 shows a partial cross-sectional view of the apparatus. In the enlarged section of FIG. 7, the distal end 46 of the filament is shown in outline to depict how this would be severed on insertion of the distal end of the feed tube 12 into the guide tube 60. Once so severed, the remainder of the distal end 46' of the filamentary material is then free to move within the lumen within the tubes 12, 60 and thus to be driven through the delivery assembly and the catheter 94 by the driving fluid (in practice being pulled along with the flow of the driving fluid).

As the distal end 46 of the filamentary material 40 is fixed to the feed tube 12 there is no risk of mis-feeding of the filamentary material into the delivery device and, moreover, there is no mechanism required to insert the distal end of the filamentary material into the catheter 94 apart from by inserting the rigid feed tube 12 into the tubular guide 60, a much simpler operation given the nature of that component.

Figure 8:
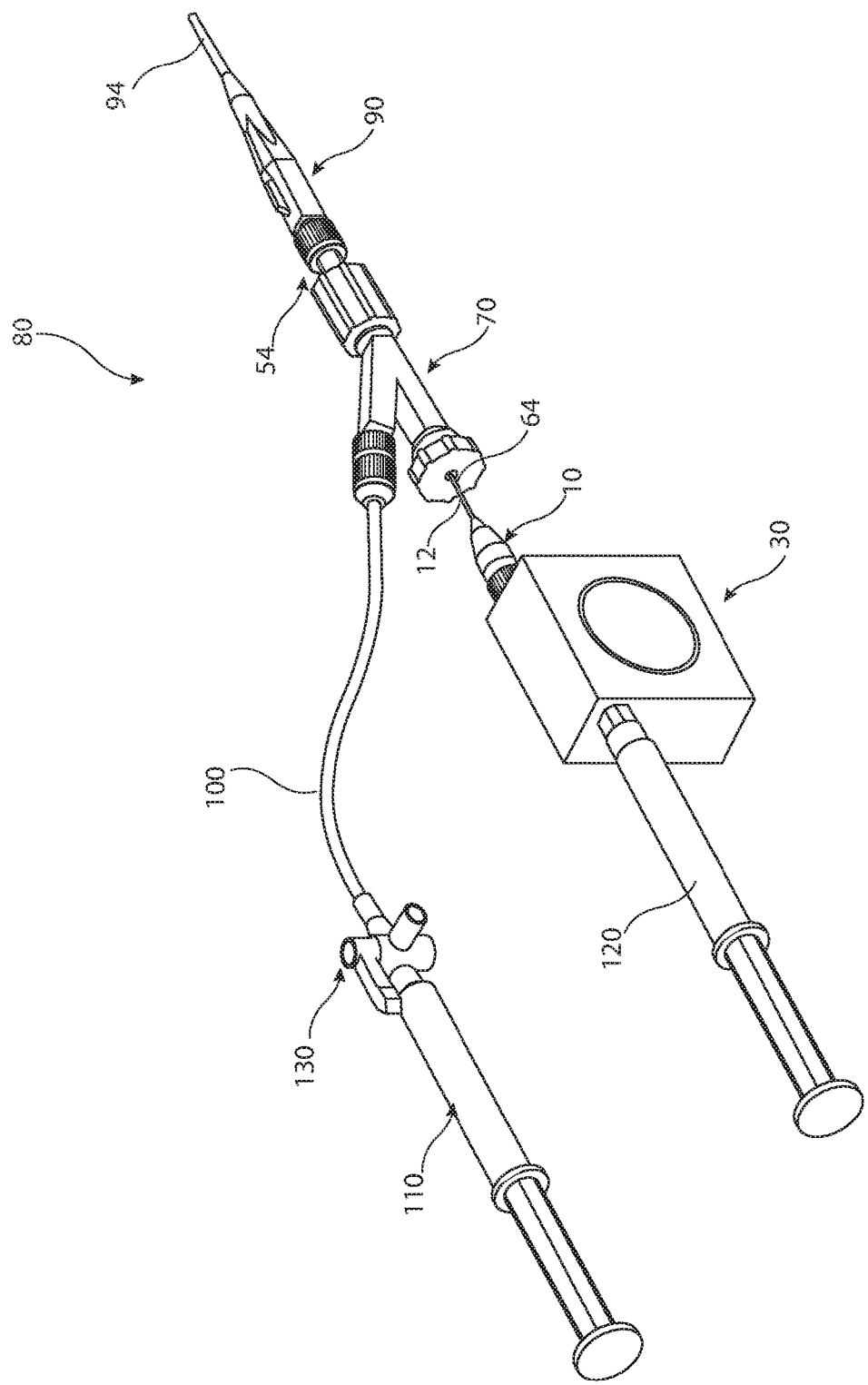
FIG. 8 is a perspective view of the apparatus in its assembled form.

FIG. 8 shows the apparatus in its fully assembled form. The filament storage device 30 is shown fitted to the feed tube assembly 10, which itself is fixed into the drive assembly 80, the latter being attached to the micro catheter assembly 90. As can be seen in FIG. 8, in this example they are provided two syringes 110, 120, for providing, respectively, driving fluid and wetting fluid. The syringe 120 provides wetting fluid for wetting the filamentary material and keeping this in a suspended state within the storage device 30, which facilitates the delivery of the filamentary material out of the storage device. The syringe 110 provides the driving fluid for feeding through the catheter assembly 90 and pulling the filamentary material with it.

A flushing valve 130 may be provided at the outlet of the syringe 110, and is closable to prevent inadvertent operation of the assembly until deployed as desired.

In this embodiment, a syringe 110 is used as the supply of driving fluid and it is considered this would be optimal in most circumstances. In other embodiments, a different source of driving fluid other than a syringe may be used, such as a fluid pump and so on.

Figure 9:
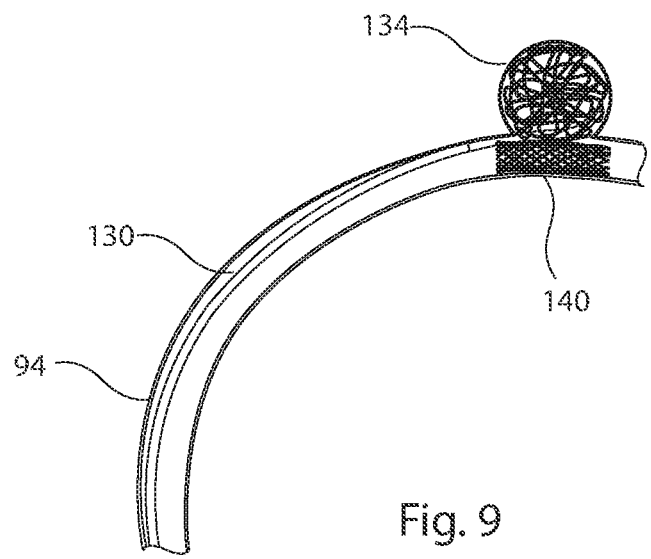
FIGS. 9 and 10 show how an aneurysm sac can be filled with filamentary material.
Figure 10:
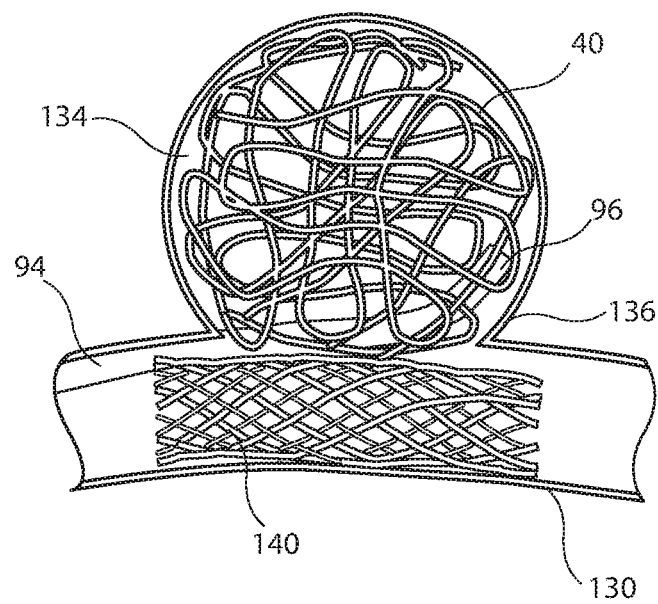

Referring now to FIGS. 9 and 10, these show two views of a vessel 130 having an aneurysm 134 therein. The aneurysm 134 forms a sack to one side of the vessel 130. A support structure, typically a stent, 140 is shown positioned across the neck 136 of the aneurysm 134 and is used to hold filamentary material within the aneurysm sack 34.

The invention claimed is:

1. Medical filament delivery apparatus including:
   a filament drive unit provided with a feed chamber, a first inlet to the feed chamber connectable to a fluid supply, a second inlet to the feed chamber connectable to a supply of filamentary material, and an outlet from the feed chamber attached to a delivery catheter;
   a tubular guide element disposed or disposable at least partially within the feed chamber and between the second inlet and the outlet; the guide element including a tubular structure with an internal lumen, the tubular guide element including a proximal end and a distal end, the proximal end having an inner first diameter; and
   an elongate filamentary material feed tube including a distal end having an outer second diameter, wherein the feed tube distal end is insertable into the proximal end of the tubular guide element, such that filamentary material from the feed tube is able to pass into the tubular guide element;
   the feed tube including a fixation member which fixes an end of filamentary material to or proximate the feed tube distal end, the fixation member providing for release of the fixed end of the filamentary material on insertion of the feed tube distal end into the proximal end of the tubular guide element.

2. Medical filament delivery apparatus according to claim 1, wherein the fixation member releases the filamentary material by severing of the fixed end of the material.

3. Medical filament delivery apparatus according to claim 1, wherein the fixation member is a slot or hole at the feed tube distal end which traps an end of filamentary material.

4. Medical filament delivery apparatus according to claim 3, wherein the feed tube distal end is a close fit in the proximal end of the tubular guide element, such that filamentary material trapped in the slot or aperture is cut when the feed tube distal end is inserted into the proximal end of the tubular guide element.

5. Medical filament delivery apparatus according to claim 1, wherein the tubular guide element includes at least one aperture therein, the at least one aperture allowing fluid in the feed chamber to flow into the internal lumen thereof.

6. Medical filament delivery apparatus according to claim 1, wherein the tubular guide element is a cannula provided with a plurality of apertures therein.

7. Medical filament delivery apparatus according to claim 1, wherein the apertures in the tubular guide element extend generally in a longitudinal direction of the tubular guide element.

8. Medical filament delivery apparatus according to claim 1, wherein the feed tube distal end includes at least one aperture therein.

9. Medical filament delivery apparatus according to claim 8, wherein the feed tube distal end includes a plurality of apertures extending generally in a longitudinal direction of the feed tube.

10. Medical filament delivery apparatus according to claim 1, including a dispenser of filamentary material, the feed tube being coupled to the dispenser.

11. Medical filament delivery apparatus according to claim 10, wherein the feed tube is attached to a casing of the dispenser and supported thereby.

12. Medical filament delivery apparatus according to claim 1, wherein the feed tube and the second inlet of the drive unit include cooperating fixation members for fixing the feed tube to the drive unit.

13. Medical filament delivery apparatus according to claim 1, including a sealing element at the outlet and/or the second inlet of the filament drive unit, whereby fluid exits the feed chamber via the lumen of the tubular guide element.

14. Medical filament delivery apparatus according to claim 1, wherein the proximal end of the tubular guide element extends beyond the second inlet of the filament drive unit.

15. Medical filament delivery apparatus according to claim 1, wherein the distal end of the tubular guide element extends beyond the outlet of the filament drive unit.

16. Medical filament delivery apparatus according to claim 15, including a delivery catheter coupled to the outlet of the filament drive unit, wherein the proximal end of the tubular guide element extends into the delivery catheter.

17. Medical filament delivery apparatus according to claim 1, wherein the tubular guide element is fitted to a coupling member, the coupling member being attachable to the filament drive unit.

18. Medical filament delivery apparatus according to claim 17, wherein the coupling member is attachable at the outlet of the filament drive unit.

19. Medical filament delivery apparatus according to claim 17, wherein the coupling member is disposed at an intermediate position along a length of the tubular guide element.

* * * * *